United States Patent [19]

Maggard

[11] Patent Number: 5,223,714
[45] Date of Patent: Jun. 29, 1993

[54] PROCESS FOR PREDICTING PROPERTIES OF MULTI-COMPONENT FLUID BLENDS

[75] Inventor: Steven M. Maggard, Barboursville, W. Va.

[73] Assignee: Ashland Oil, Inc., Ashland, Ky.

[21] Appl. No.: 797,832

[22] Filed: Nov. 26, 1991

[51] Int. Cl.$^5$ ..................... G01N 21/35; G01N 21/59
[52] U.S. Cl. ................................. 250/343; 250/339; 436/55
[58] Field of Search ................ 250/341, 339, 343; 436/55

[56] References Cited

U.S. PATENT DOCUMENTS

| | | | |
|---|---|---|---|
| 4,277,326 | 7/1981 | Schlosberg et al. | 208/263 |
| 4,323,777 | 4/1982 | Baskins et al. | 250/339 |
| 4,433,239 | 2/1984 | Thompson | 250/255 |
| 4,591,718 | 5/1986 | Amer | 250/339 |
| 4,800,279 | 1/1989 | Hieftje et al. | 250/339 |
| 4,963,745 | 10/1990 | Maggard | 250/343 |

FOREIGN PATENT DOCUMENTS

| | | | |
|---|---|---|---|
| 285251 | 10/1988 | European Pat. Off. | 250/343 |
| 0304232 | 2/1989 | European Pat. Off. | |

OTHER PUBLICATIONS

Kelly et al, "Prediction of Gasoline Octane Numbers from Near Infrared Spectral Features in the Range 660–1215 nm", Analytical Chemistry, vol. 61, No. 4, Feb. 15, 1989, pp. 313–320.

Kelly et al, "Nondestructive Analytical Procedure for Simultaneous Estimation of the Major Classes of Hydrocarbon Constituents of Finished Gasolines", Analytical Chemistry, vol. 62, No. 14, Jul. 15, 1990 pp. 1444–1451.

"Advances in Near Infrared Analyzer Technology", Dr. H. Mark & Dr. G. Kemeny, Chemical Processing, Feb. 1991.

LT Application Note, Industry: Petroleum; "Determination of Octane Number by NIR", LT Industries, Inc., Rockville, Md. (~1989).

"Near-Infrared Reflectance Analysis by Gauss-Jordan Linear Algebra", by D. E. Honigs et al., Applied Spectroscopy, vol. 37, No. 6, 1983.

Primary Examiner—Constantine Hannaher
Assistant Examiner—Edward J. Glick
Attorney, Agent, or Firm—Richard C. Willson, Jr.

[57] ABSTRACT

The octane of components used in the blending of gasoline is used to predict the octane of the finished gasoline blend by measuring absorbances, preferably in the near-infrared range, and metering the fraction of each blending component as independent variables and performing a multiple regression on the data modeling the dependent variable of the various octanes. Percent aromatics in diesel fuel and other finished chemical or physical properties of the finished blend can be controlled by feed-forward and/or feed-back techniques.

13 Claims, 6 Drawing Sheets

PROCESS FOR PREDICTING PROPERTIES OF MULTI-COMPONENT FLUID BLENDS

Cross References to Related Applications

Cross references to related applications, U.S. Ser. No. 506,391, filed Apr. 9, 1990, U.S. Ser. No. 698,411, filed May 10, 1991, U.S. Ser. No. 626,132, filed Dec. 11, 1990, now U.S. Pat. No. 5,145,785, issued Sep. 8, 1992, relates to the general field of the present invention.

Background of the Invention

I. Field of the Invention:

The present invention relates to the prediction of finished physical or chemical properties in blended products from measurements made in the preblended components, generally classified in the U.S. Patent and Trademark Office, Classification Class 250, Subclass 339 or 343 or International class/GO1J 1/00 or GO1N 21/59.

II. Description of the Prior Art

U.S. Pat. No. 4,800,279 to Hieftje et al., issued Jan. 24, 1989, teaches use of near-infrared (NIR) to predict physical properties of certain hydrocarbon mixtures.

M. H. Rusin, H. S. Chung and J. F. Marshall, A "Transformation" Method for Calculating the Research and Motor Octane Numbers of Gasoline Blends 20 Ind. Eng. Chem. Fundam. 195-204 (1981), M. H. Rusin, H. S. Chung, and J. F. Marshall teaches octane blending interaction by use of data transformation to arrive at a linear model for blending, a procedure which has become well-adopted in the petroleum industry for the blending of fuels having specific octanes.

E. P. Patent 0,285,251 to Lambert (Assigned BP Oil) teaches NIR absorption in the wave number spectral range from 6667 to 3840 cm−1 (1500-2604 nanometers) by spectrometer with optional fiber optics and computer and suggests determining octane number of each storage tank to calculate proportions of product for transferring to the mixing tank, but does not teach an actual method for predicting the octane of the final product.

Kelly, Barlow, Jinguji and Callis of the University of Washington, Seattle, *Prediction of Gasoline Octane Numbers from Near-Infrared Spectral Features in the Range 660-1215 nm* (Analytical Chem. 61, 313-320,) found octane numbers of finished blends of gasoline are indicated by near-infrared absorbance in the range 660-1215 nanometers (nm). They found best correlation between absorbance and octane number to occur at 896, 932 and 1164 nm for research octane number (RON) 930, 940 and 1012 nm for motor octane number (MON), and 896, 932 and 1032 nm for pump octane number (PON).

In the inventor's doctoral dissertation, *A Chemometric Analysis of a Magnetic Water Treatment Device* available from University Microfilms International, Dissertation Information Service, order number 8919928, there is a discussion of linear regression analysis (simple and multiple) for a linear regression model, and data transformations which can transform non-linear types of data into data which is appropriate for linear regression modeling. Definitions are shown which establish the degree of reliability that the value of one variable (the dependent variable) can be estimated on the basis of values for other variables (the independent variables). In general, the methods for determining regression constants (or coefficients) for the calibration equations discussed in the inventor's doctoral thesis are useful in establishing the calibration equation for the first or reference instrument in the present invention.

U.S. Pat. No. 4,963,745 to Maggard teaches measurement of octane by preferred bands in the near-infrared region.

*Nondestructive Analytical Procedure for Simultaneous Estimation of the major Classes of Hydrocarbon Constituents of Finished Gasolines*, by Kelly et al., Anal. Chem. 1990, 62, pages 1444-1451, teaches the determination of saturates, aromatics, and olefins for finished gasolines only. This Kelly article teaches methods similar to U.S. Ser. No. 506,391, filed Apr. 9, 1990, but with poorer results, which Kelly claims are due to the primary reference method.

*Determination of Gasoline Octane Numbers from Chemical Composition*, M. E. Myers, Jr., J. Stollsteimer, and A. M. Wims, *Analytical Chemistry*, 47(13), 2301, concerns the use of proton NMR spectra to predict the octane number of finished gasoline blends. It discloses use of proton NMR to determine the isoparaffin index (the ratio of $CH_3:CH_2$) and aromatic content of gasoline. The isoparaffin index and aromatic content determined by NMR are then used with lead content and sulfur content to predict octane via multiple linear regression with a large standard error of 1.1 octane numbers for both RON and MON.

Myers shows that the isoparaffin index and aromatic content are determined by integrating NMR spectral peaks, the frequencies of which are constant as measured by chemical shifts from a tetramethyl silane (TMS) standard. Hence, their approach could be loosely associated with our preferred use of isonumeric wavelengths.

There are important distinctions between the article and our invention, however. The present invention uses isonumeric wavelengths to measure octane on dissimilar substances, not a single substance as shown by Myers. The present invention does not require other types of measurements; e.g., lead and sulfur content, be combined with our isonumeric wavelength data, or even that we have to use isonumeric wavelengths. The speed of acquisition of NMR data, the sulfur analysis, and the necessary sample dilution, all combine to make the Myers NMR method unsuitable for process control as well.

Myers et al, *Determination of Gasoline Octane Numbers from Chemical Composition* 47 Anal. Chem 2301-2304 (1975) showed the correlation between chemical structure of gasoline components and the octane of the end-product gasoline was not strictly linear.

None of the above references is understood to teach a method for the prediction of chemical or physical properties, such as octane of preblending components from absorbances of preblending components, such as near-infrared with prediction of the property in the finished blend by the simple weighted linear additive technique of the present invention.

Summary of the Invention

I. General Statement of the Invention

According to the invention, the property of a fluid blend (e.g., octane of a gasoline blend) is predicted and controlled by measuring the absorbances (e.g., NIR is preferred for octane), then converting these to signals, then manipulating these signals (preferably taking the first derivative, or higher derivative in the case of NIR), and weighting each signal according to the weight or volume of that component to be used in the final blend, then adding substantially linearly the weighted octane contribution of each blending component to arrive at a final estimate of the gasoline. Preferably these signals are used to control the blending process through well-known techniques of feed-forward and/or feed-back control. The immediacy and simplicity provided by the invention allows previously unattained practical control systems for blending of liquid components such as gasolines.

II. Utility of the Invention

The invention is useful for controlling the blending of a wide variety of fluids, including gases such as natural gas, butane, propane, etc., in their gaseous state, and more preferably, liquids such as butane and propane in their liquid state, alcoholic and non-alcoholic beverages, sauces, soups and other liquid food stuffs, pharmaceuticals, detergents and other cleaning compositions, and most preferably, hydrocarbons used for fuels, especially those used for fuels such as jet fuels, diesel fuels, and most preferably, gasoline of pre-determined octane number. The absorbances used with the invention can include transflectance, transmittance, reflectance (including diffuse, specular, attenuated, total, etc.,) and other fluorescences, phosphorescences, and other luminosities, emissions, and particularly preferred, near-infrared absorbances and transflectances. The invention is particularly preferred for controlled systems where its simplicity and immediacy offer previously unknown ability to control the flow of blending components to create batches or continuous streams of blended fluid product having a pre-set physical property such as octane.

DESCRIPTION OF THE PREFERRED EMBODIMENTS

EXAMPLE 1

Blending diesel fuel by the process of the invention

Figure 1:
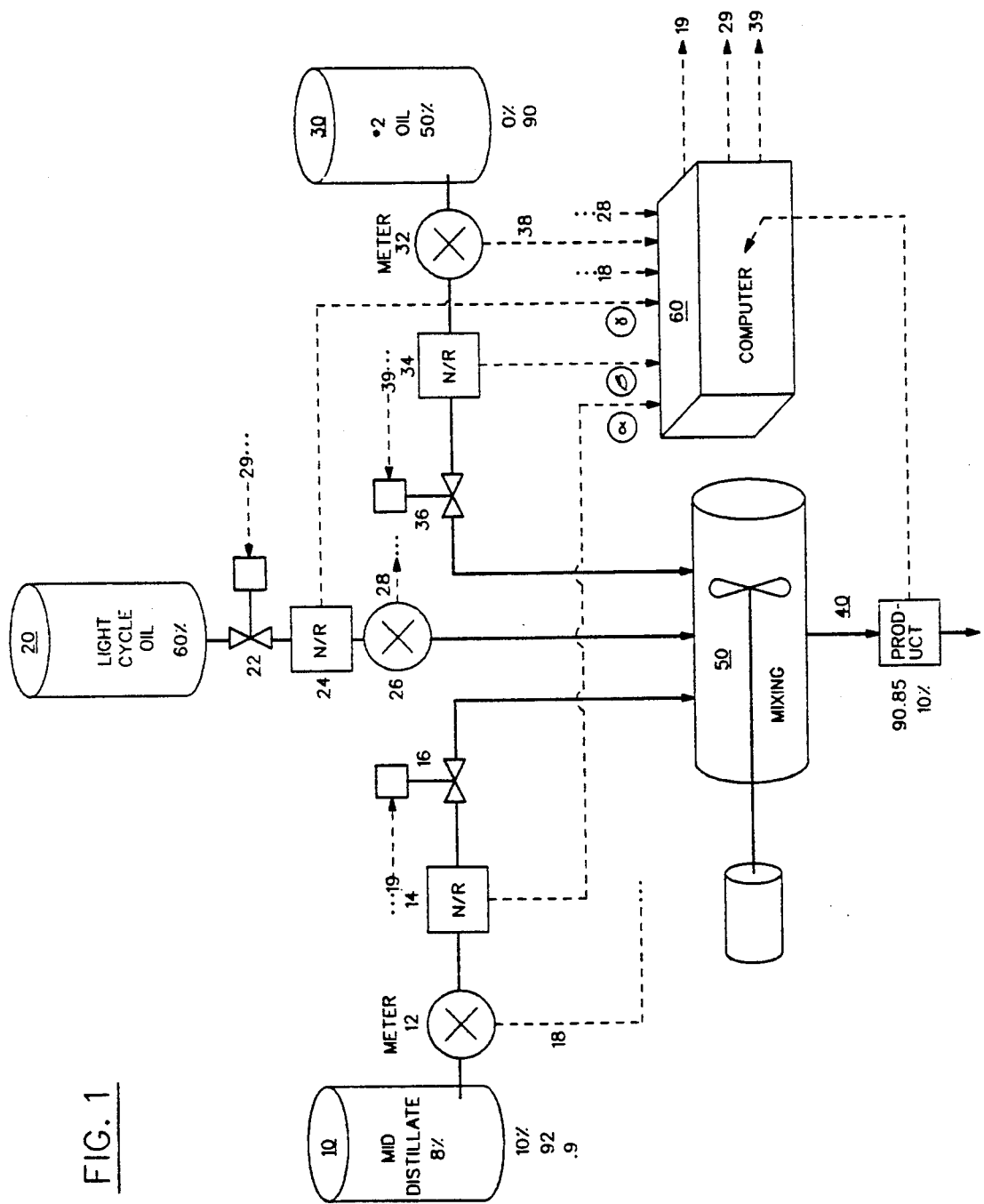
FIG. 1 is a block-flow diagram of the steps of a preferred embodiment of the invention, showing the control valves, absorbance measuring devices, meters, mixers, computers, etc. for a preferred embodiment of the invention used in fuel blending.

Referring to FIG. 1, a tank of mid-distillate fuel 10, is to be the primary blending stock to be blended with light-cycle oil and No. 2 oil to form a product 40 in a mixing tank 50. The product, diesel fuel, is required to have a maximum of 10% (by volume) aromatic content, and cheaper light-cycle oil 20 and No. 2 oil 30 are added to increase the aromatic content of the finished product 40 to near the 10% maximum. The mid-distillate has 8% aromatics content; the light-cycle oil has 60% aromatics content; and the No. 2 oil has 50% aromatics content in this example, and, because of differences in average molecular weight and density, their aromatics contents (by volume) does not add linearly. In operation, mid-distillate 10 flows through meter 12, through NIR absorbance measuring device 14, and finally through control valve 16, and the light-cycle oil flows through control valve 22, NIR device 24, and meter 26, while the No. 2 oil flows through meter 32, NIR device 34, and control valve 36. Meter 32 emits a signal 38 indicative of the volume of mid-distillate flowing into the mixing tank 50 and similar meters 26 and 12 emit analogous signals 28 and 18, indicative of their respective volumes of flow. The three NIR devices 14, 24, and 34, emit respectively, signals (alpha, gamma, and beta), indicative of the respective near-infrared absorbances (related to aromatic content) of the mid-distillate, No. 2 oil and light cycle oil, respectively, which are fed to computer 60.

Figure 2:
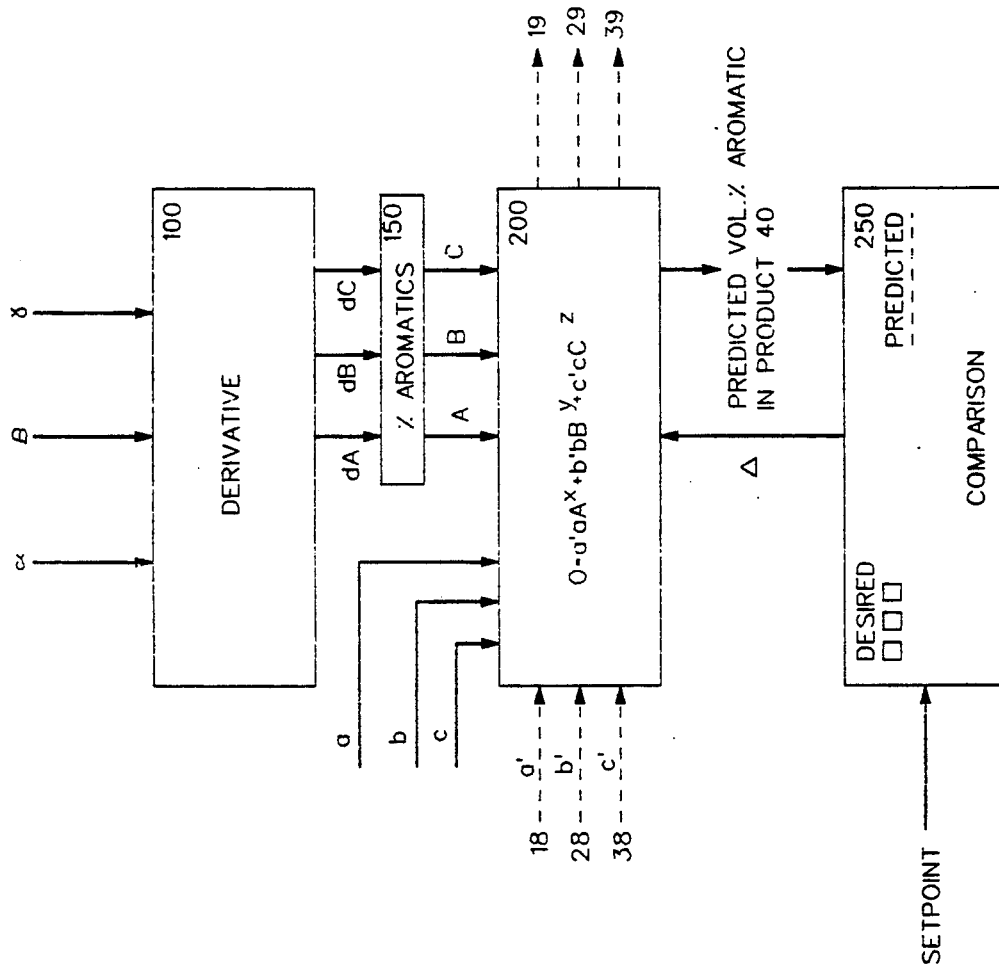
FIG. 2 is a block diagram of the mathematical manipulations performed by the computer shown in FIG. 1 to arrive at the various control signals which provide the product having the pre-set physical property, in this case, diesel fuel having substantially precisely 10% aromatics by volume.

Referring now to FIG. 2, absorbance signals alpha, beta, and gamma, are first converted to their mathematical derivatives in step 100. This may be the direct signal or the first, second, third, etc. derivative, whichever has been found optimal for the components to be blended. In this particular case of diesel fuel production, the second derivative has proven optimal. With oxygenated fuel, such as ethanol, the first derivative may be preferred.

The derivative signals, dA, dB, and dC are fed to step 150 which figures the respective percent aromatics, A, B and C, which are inputted to step 200 described below.

The resulting three volume % aromatic concentration signals A, B and C are fed to step 200, which solves the equation:

$$O = K + a'aA^x + b'bB^y + c'cC^z$$

O = vol % aromatic in product = constant + Σ[(vol % of component in blend)(weighting constant of each component)(aromatic content of each component)]

Where A, B, C, are respective aromatic concentrations of each of a series of tanks; and a, b, c, are the regression weighting constants for each of the respective components, a', b', c', are the volume percent of each component being added to the blend (or weight or flow rate). In general, we have found that when (alpha, beta, and gamma) are expressed in terms of the NIR absorbance, or derivatives of NIR absorbance, (or transflectance or derivatives of transflectance, etc.) then x, y, and z are substantially equal to one, thus rendering the equation first-order and greatly simplifying its solution.

In step 200, a', b' and c' are supplied by signals 18, 28 and 38 from volumetric meters 12, 26 and 32, respectively.

Signals a, b and c are weighting constants which are input from results of a previous calibration, preferably using the components which are to be blended in this example. To determine these values, a set of samples of mid-distillate, light-cycle oil, and No. 2 fuel oil are mixed in known proportions and the aromatic content of each component and each final blend are determined by standard techniques. The near-infrared absorbance spectra of each component is measured, converted to second derivative of absorbance, and statistically analyzed by multiple linear regression, partial least squares, principal component regression, etc., to find wavelengths which correlate with the property—here volume percent aromatic content. Once these wavelengths are determined, alpha, beta and gamma are defined and likewise dA, dB and dC. The values A, B, and C are determined by calculation—in accordance with the appropriate statistical technique—and correspond to the volume percent aromatic content of each component as predicted from its near-infrared absorbance spectrum, the error of which was statistically minimized by substituting into the equation shown in step 200, the calculated values A, B, C (or actually measured values), the volume percent of each component a', b', c', and the actually measured (or predicted) volume % aromatic content of the blend for 0, one can determine the regression weight constants a, b, c, since they are the only unknowns. Note that x, y and z are each substantially equal to one, so that the equation itself is substantially linear. So the equation is readily solved linearly. For unknown concentrations, the result is an output of signals 19, 29 and 39, which reset flow-control valves 16, 22 and 36, respectively. So not wishing to be bound by any particular theoretical explanation of the invention, it seems possible that the linearity of x, y and z is made possible by proper selection of near-infrared absorbances, alpha, beta and gamma. When properly selected by use of a set of isonumeric wavelengths, the functional groups contributions to the predicted property can add substantially linearly.

An additional output from step 200 is a signal indicative of predicted volume percent aromatic in product 40. This signal can be optionally displayed and is inputted to step 250, a comparison which compares the predicted volume percent aromatic signal with the set point (entered manually or by electronic means) of the level at which the blended physical property is to be maintained, e.g., 9.9% aromatics in the present example. From this comparison, a signal, delta, is input back to control valves 16, 22 and 36 to form a closed loop which automatically readjusts the value of 0 toward the set point level. After a few iterations, this closed loop will generally bring the controlled value of 0 within very close tolerance with the set point value.

It will be noted that the present invention utilizes feed-forward control; i.e, analysis of the individual components to predict the value of the physical property in the finished blend. Alternatively, the finished blend could be measured and the result fed back, more conventionally, to control the amounts of components. However, in three-component blends, particularly where economic optimization based on the costs of the individual components is desired, feed-forward is well recognized to have substantial control advantages. Still more preferably, in complex mixtures, the techniques of both feed-forward and feed-back can be combined, e.g., by inputting the feed-back signal in place of the comparison signal, delta, either constantly or intermittently.

It should be understood that the above description of FIG. 2 is conceptual only, and that all of the steps 100, 150, 200 and 250 will normally take place within a single computer 60, as shown in FIG. 1, or with a PC linked to a central computer that controls the process. The step-by-step block diagram of FIG. 2 is presented as an aid to understanding the mathematical manipulations involved in the invention.

EXAMPLE 2

Blending of gasoline components to provide desired octane in the finished blend

Using the general techniques described in Example 1, and as an improvement on the techniques described in my U.S. Pat. No. 4,963,745, gasolines are blended as shown in FIG. 3.

The steps in FIG. 2 apply also to this example, except that the inputs are related to the octanes of the individual components and the octane of the final blend. Table A shows the research octane minima and maxima for a series of gasoline components which is input into the computer 60. This information is combined with the volume fraction of each component summarized in Table B and the finished blend gasoline octane for a series of blends from these components to determine the weighting constants for each component.

Figure 3:
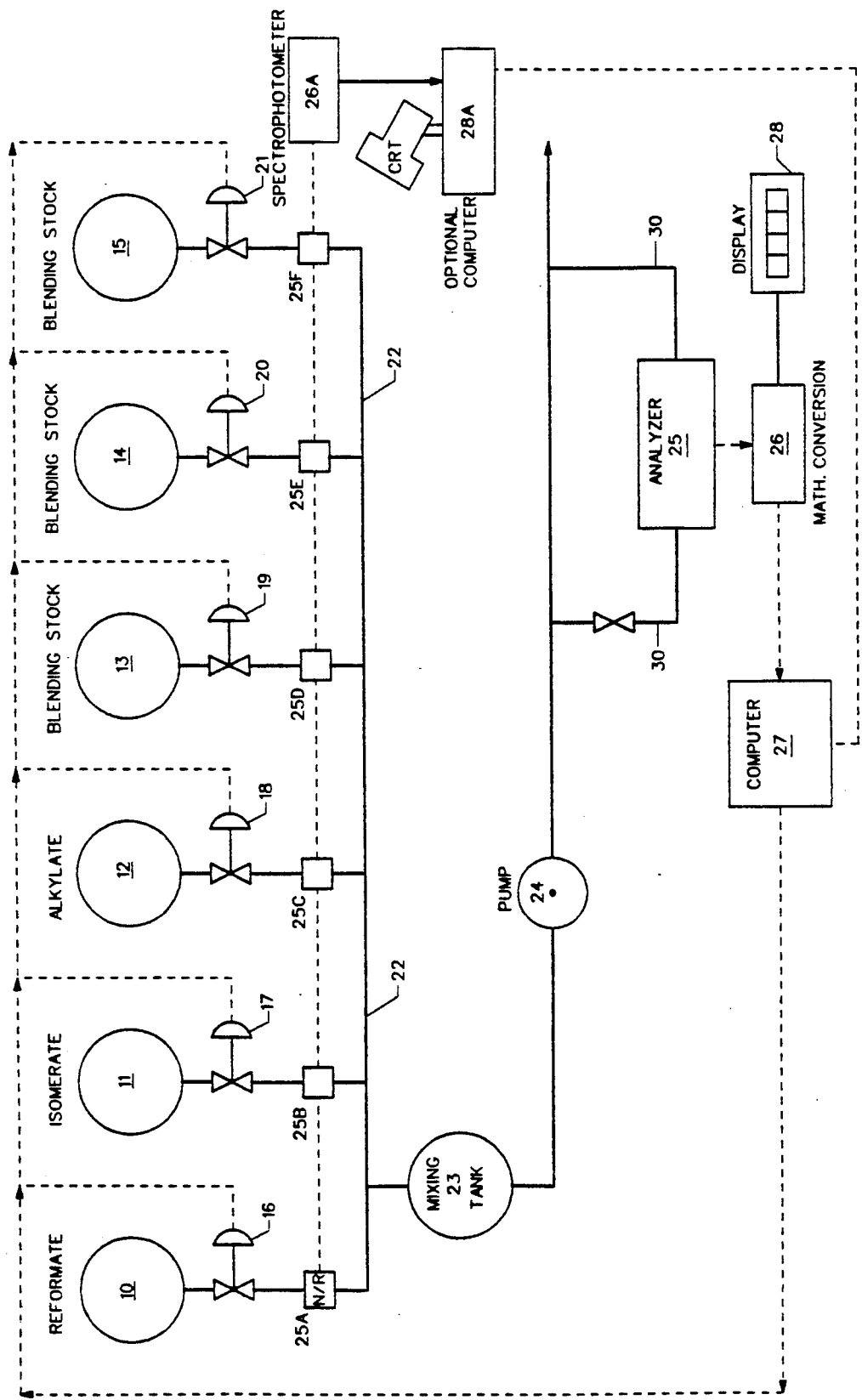
FIG. 3 is a schematic diagram of the process of Example 2.

FIG. 3 shows schematically the 10-component blending system utilized in this example. Tanks 10 through 15 contain gasoline blending stocks; e.g., reformates, isomerates, alkylates, etc., each of these components has its own octane value as well as a price. For example, reformate and alkylate are both high in octane number but are relatively expensive blending stocks. Each of the tanks has an automatic control valve 16 through 21 which controls the flow of the particular blending stock from the tank into a common header 22 and then sent to mixing tank 23 from which pump 24 moves the blended gasoline through on-line analyzer 25 which analyzes the near-infrared absorbance of a side stream 30 and transmits the resulting absorbance of a measurements to a mathematical conversion device 26 which converts the signal into the second derivative, calculates an octane, and feeds the resulting signal to computer 27. Optional display device 28 can display both the target octane and the measured octane number at all times. The output from computer 27 according to the present invention is now supplemented by a "feed-forward" signal obtained from a second (or the same) NIR spectrophotometer 26A which inputs data from absorbance measuring cells 25A through 25F, in sequence through fiber optics connecting the spectrophotometer with the individual cells, sequentially; e.g., by multiplexing. Spectrophotometer 26A process the signal and displays sequentially the octane (pump, motor, and/or research) numbers of the individual blending stocks on computer display 28A which also outputs a signal to the main computer 27. Thus the blending system enjoys both feed-back (as described in my above U.S. Patent) and additionally, according to the present invention, feed-forward by analysis of the individual blending stocks, modeled under the techniques of the present invention as shown in FIG. 2 (except that there are ten components, rather than three).

For simplicity, the input and the output signals are shown for only one component but similar and analogous signals are used for each of the individual 10 components. The system is capable of blending a wide variety of fuels, including sub-octane unleaded gasoline, having a pump (R+M/2) octane of 84.7, primarily used as a blending component for blending with higher octane up to octanes as high as 93.5 pump octane. Other components have pump octane numbers of 30 to as high as 130. The optimizing of these components, primarily on the basis of component cost, Reid vapor pressure contribution, benzene content, total aromatic content, olefin content, end boiling point, percent oxygenate, and other criteria which are desired because of motorists' preferences or required because of government regulations, can be controlled and optimized.

This combination of feed-forward plus feed-back inputting of both octane values and price values provides an economically optimized, highly constant blend with fail-safe features because of the ability of either the feed-forward or the feed-back system to control the blend by itself.

EXAMPLE 3

Prediction of research octane of blend from research octanes of components

Table A shows the maximum and minimum research octane of ten individual components for a series of 34 gasoline blends as measured by near-infrared analysis according to the techniques of U.S. Pat. No. 4,963,745 to Maggard. Note that butane and MTBE have been assigned constant octane values. The maximum and minimum fraction of each component used in the series of 34 blends is shown for each in Table B.

Figure 4:
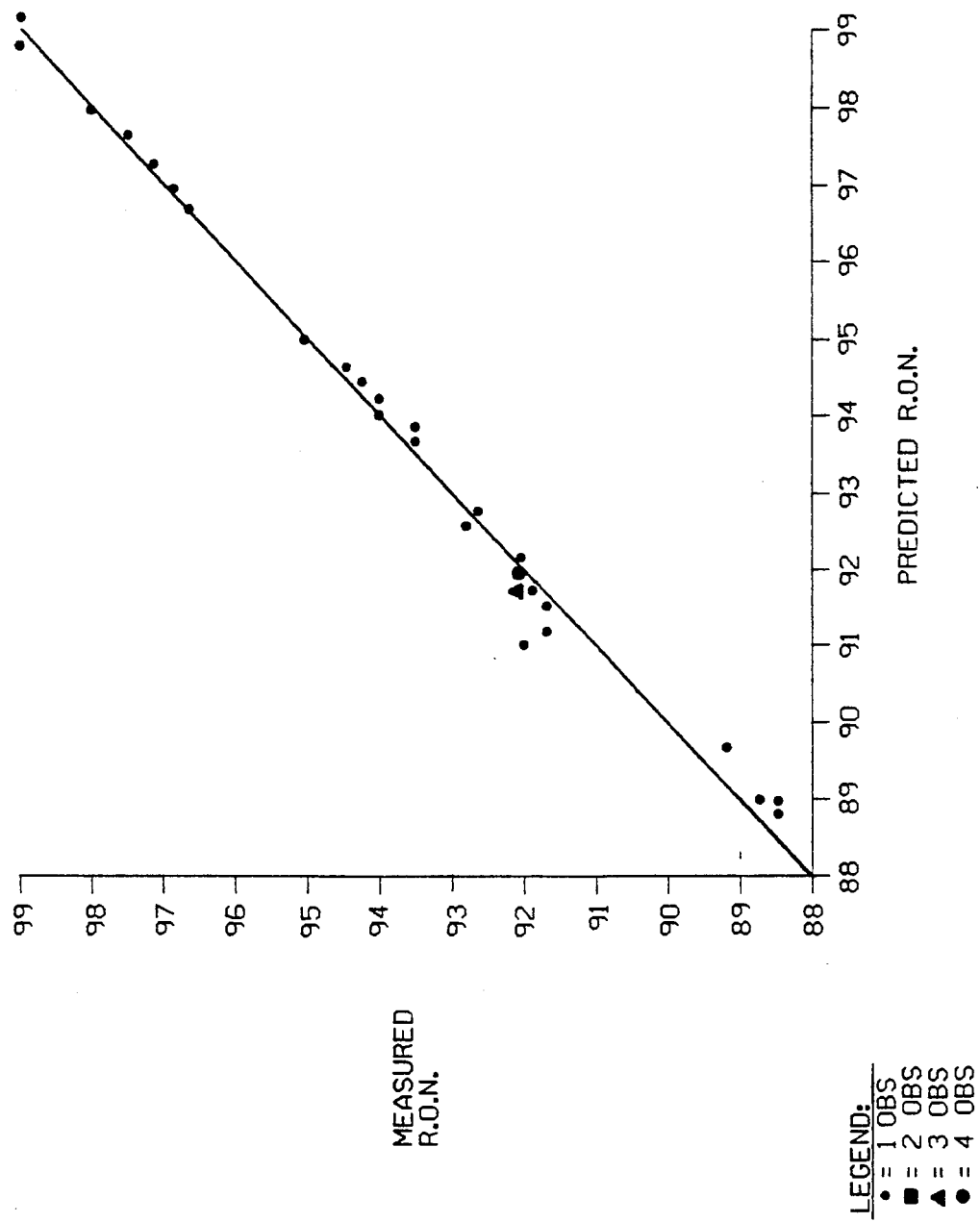
FIG. 4 is a plot of measured research octane versus RON predicted by the invention.

Using the techniques of Example 2, the research octane for each of the blends is mathematically predicted and plotted as the abscissa of FIG. 4, while the actual research octane number of each of the finished blends was measured by knock-engine, the standard ASTM test D2699, and plotted as the ordinate in FIG. 4.

As can be seen from FIG. 4, the mathematical prediction shows excellent agreement with the actual laboratory knock-engine data of the finished blends. Further, the correlation is substantially linear over a wide range of from about 88 to 100 research octane number. The standard error, Se, is 0.334 research octane numbers with a confidence of plus or minus one sigma. This compares favorably with the one sigma error for the above ASTM standard method which is 0.40. Similarly, the correlation co-efficient is 0.9957 indicating excellent correlation between the research octane number as mathematically predicted from the techniques of the present invention with the standard ASTM research octane number as determined for the finished blend. (It should be noted that in Examples 3, 4, and 5, raffinate was assigned two different values depending on whether it was preblended into suboctane number blends which were in turn blended into the finished gasoline blend or whether the raffinate was blended directly into the finished gasoline blend.)

EXAMPLE 4

Prediction of motor octane of blend from motor octanes of components

Using techniques similar to those of Example 3, Table C shows the ten blending components which are used to construct a set of 34 finished gasoline blends, together with the maximum and minimum of the motor octane numbers of the individual components. Note again that butane and MTBE have been assigned constant octane values.

Figure 5:
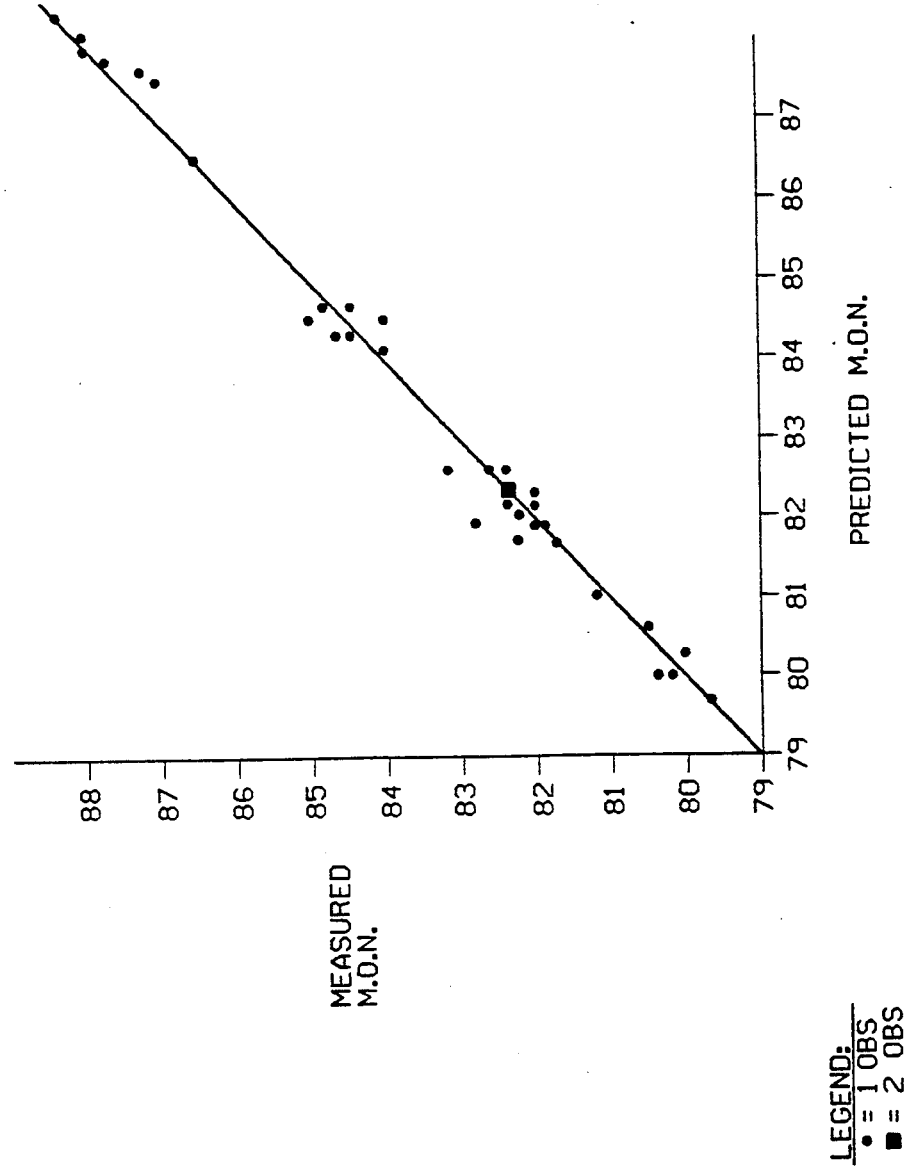
FIG. 5 is a plot of measured motor octane versus MON predicted by the invention.

Table B again shows the range of fractions of the component used in each of the blends and FIG. 5 shows the correlation between the predicted (abscissa) and the measured (ordinate) motor octane number as measured by ASTM method D2700.

Again standard error is found to be 0.363 (as compared to the ASTM method standard error of 0.6) motor octane numbers within plus or minus one sigma; the correlation is an excellent 0.993. Note that raffinate was again assigned two values, depending on blend type, as in Example 3.

EXAMPLE 5

Prediction of pump octane of blend from pump octanes of components

Using techniques similar to those of Example 3, Table D shows the ten blending components which are used to construct a set of 34 finished gasoline blends, together with the maximum and minimum of the pump [(R+M)/2] octane numbers of the individual components.

Figure 6:
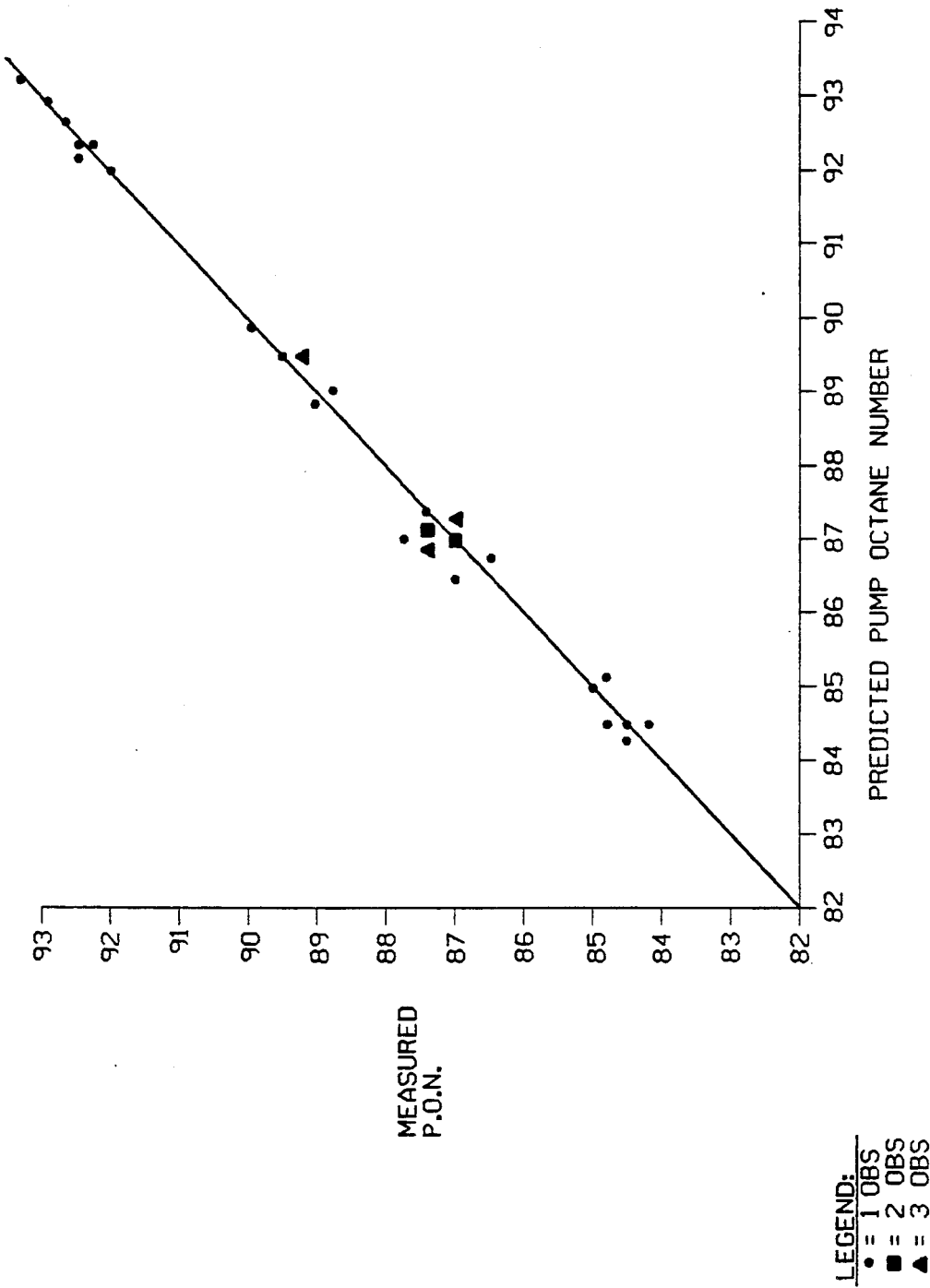
FIG. 6 is a plot of measured pump octane versus PON predicted by the invention.

Table B again shows the range of fractions of the component used in each of the blends and FIG. 6 shows the correlation between the predicted (abscissa) and the measured (ordinate) pump octane number as measured by average of ASTM 2700 and 2699.

The standard error is found to be 0.287 (as compared to the ASTM method standard error of 0.36 pump octane numbers within plus or minus one sigma; the correlation is an excellent 0.996. [Note the octanes of butane and MTBE are assumed constant and raffinate are again given two values depending on blend type as in Example 3]).

MODIFICATIONS

Specific compositions, methods, or embodiments discussed are intended to be only illustrative of the invention disclosed by this specification. Variation on these composition, methods, or embodiments are readily apparent to a person of skill in the art based upon the teachings of this specification and are therefore intended to be included as part of the inventions disclosed herein. For example, cetane number cost factors can be inputted to computer 60 to determine optimum (lowest) cost for finished product having the required properties. Trial will reveal which derivative, first, second, etc., if any is optimal for each set of components to be blended. Though preferred analysis is by NIR, knock-engine or other values can be inputted and used with the mathematical prediction techniques of the invention. Also the techniques of the invention can be applied to determine boiling point and end boiling point of the hydrocarbons or vapor pressure (preferably Reid Vapor Pressure). In preferred embodiments, the absorbances of the components are isonumeric.

Reference to U.S. patents made in this specification is intended to result in such U.S. patents being expressly incorporated herein by reference.

TABLE A

| VARIABLE | N | MINIMUM VALUE | MAXIMUM VALUE |
|---|---|---|---|
| R1727 MTBE | 34 | 110.000 | 110.000 |
| R1732 Heavy Reformate | 34 | 104.973 | 128.461 |
| R1736 Butane | 34 | 92.000 | 92.000 |
| R1765 Raffinate | 34 | 44.729 | 84.364 |
| R1766 Light Cat Crack | 34 | 92.937 | 93.281 |
| R1811 Alkylate | 34 | 93.740 | 95.431 |
| R1812 Whole Reformate | 34 | 90.348 | 99.474 |
| R1817 DSN | 34 | 35.317 | 78.177 |
| R1856 | 34 | 90.931 | 92.278 |

TABLE A-continued

| VARIABLE | N | MINIMUM VALUE | MAXIMUM VALUE |
|---|---|---|---|
| Heavy Cat Crack R1859 Isomerate | 34 | 73.018 | 84.193 |

TABLE B

| VARIABLE | N | MINIMUM VALUE | MAXIMUM VALUE | RANGE | MEAN | STANDARD DEVIATION |
|---|---|---|---|---|---|---|
| F727 MTBE | 34 | 0.0000 | 0.1764 | 0.1764 | 0.0134 | 0.0420 |
| F732 Heavy Ref | 34 | 0.0000 | 0.3078 | 0.3078 | 0.0454 | 0.0640 |
| F736 Butane | 34 | 0.0023 | 0.0676 | 0.0652 | 0.0338 | 0.0133 |
| F765 Raffinate | 34 | 0.0000 | 0.0518 | 0.0518 | 0.0074 | 0.0158 |
| F766 LCC | 34 | 0.0000 | 0.1246 | 0.1246 | 0.0100 | 0.0327 |
| F811 Akly | 34 | 0.0000 | 0.4459 | 0.4459 | 0.1219 | 0.1486 |
| F812 Whole Ref | 34 | 0.1006 | 0.4113 | 0.3106 | 0.1894 | 0.0697 |
| F817 DSN | 34 | 0.0000 | 0.0883 | 0.0883 | 0.0099 | 0.0217 |
| F856 HCC | 34 | 0.1845 | 0.7045 | 0.5200 | 0.4836 | 0.1330 |
| F859 Isom | 34 | 0.0000 | 0.2401 | 0.2401 | 0.0796 | 0.0702 |
| F7652 Raffinate | 34 | 0.0000 | 0.0721 | 0.0721 | 0.0049 | 0.0169 |

TABLE C

| VARIABLE | N | MINIMUM VALUE | MAXIMUM VALUE |
|---|---|---|---|
| R1727 MTBE | 34 | 110.000 | 110.000 |
| R1732 Heavy Ref | 34 | 98.721 | 112.861 |
| R1736 Butane | 34 | 90.000 | 90.000 |
| R1765 Raffinate | 34 | 39.529 | 57.743 |
| R1766 LCC | 34 | 79.626 | 80.079 |
| R1811 Alky | 34 | 91.576 | 93.819 |
| R1812 Whole Ref | 34 | 81.170 | 88.335 |
| R1817 DSN | 34 | 37.702 | 69.063 |
| R1856 HCC | 34 | 79.572 | 79.879 |
| R1859 Isom | 34 | 77.235 | 80.368 |

TABLE D

| VARIABLE | N | MINIMUM VALUE | MAXIMUM VALUE |
|---|---|---|---|
| R1727 MTBE | 34 | 110.000 | 110.000 |
| R1732 Heavy Ref | 34 | 98.168 | 122.678 |
| R1736 Butane | 34 | 91.000 | 91.000 |
| R1765 Raffinate | 34 | 50.048 | 64.675 |
| R1766 LCC | 34 | 86.396 | 86.689 |
| R1811 Alky | 34 | 92.181 | 94.597 |
| R1812 Whole Ref | 34 | 84.627 | 93.962 |
| R1817 DSN | 34 | 34.738 | 71.131 |
| R1856 HCC | 34 | 85.151 | 86.011 |
| R1859 HCC Isom | 34 | 74.242 | 83.447 |

I claim:

1. A process for controlling the blending of a plurality of fluid components comprising in combination the steps of:
   a) measuring an absorbance at selected wavelengths in the infrared indicative of a property of each of said plurality of fluid components to be blended together;
   b) outputting a signal indicative of each said absorbance for each of said components;
   c) optionally converting said absorbance signal indicative of said property to a first or higher mathematical derivative signal;
   d) weightedly adding substantially linearly the absorbance signals or the first powers of said derivative signals to provide a signal indicative of the blended value of said property after said components are blended together;
   e) controlling the quantity of said plurality of fluid components in response to said signal indicative of said blended value.

2. A process according to claim 1 wherein said absorbance signal is converted to a first or higher derivative and the first powers thereof are weightedly added.

3. A process according to claim 1 wherein said absorbance comprises absorbance measured in the near-infrared range.

4. A process according to claim 1 wherein said components are fuels.

5. A process according to claim 1 wherein said property is boiling point.

6. A process according to claim 1 wherein said property is end boiling point.

7. A process according to claim 1 wherein said property is octane.

8. A process according to claim 1 wherein said property is cetane number.

9. A process according to claim 1 wherein said property is aromatic content.

10. A process according to claim 1 wherein said property is olefin content.

11. A process according to claim 1 wherein said absorbances of said plurality of fluid components are isonumeric for each component.

12. A process according to claim 1 wherein said property is vapor pressure.

13. A process according to claim 1 wherein said property is Reid Vapor Pressure.

* * * * *